(12) United States Patent
Walsh et al.

(10) Patent No.: US 6,802,857 B1
(45) Date of Patent: Oct. 12, 2004

(54) MRI STENT

(75) Inventors: Edward G. Walsh, Irondale, AL (US); Ramakrishna Venugopalan, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 442 days.

(21) Appl. No.: 09/685,098

(22) Filed: Oct. 11, 2000

(51) Int. Cl.[7] ................................................. A61F 2/06
(52) U.S. Cl. ................................................. 623/1.15
(58) Field of Search ........................... 623/1, 1.11–1.23, 623/1.43, 900; 606/159, 32, 33, 36, 37, 39, 194, 191; 600/505, 462, 468

(56) References Cited

U.S. PATENT DOCUMENTS

| | | | | |
|---|---|---|---|---|
| 5,676,685 A | * | 10/1997 | Razavi | ........................ 606/194 |
| 5,980,563 A | * | 11/1999 | Tu et al. | ........................ 606/41 |
| 6,053,873 A | * | 4/2000 | Govari et al. | ................ 600/505 |
| 6,170,488 B1 | * | 1/2001 | Spillman, Jr. et al. | ...... 128/899 |
| 6,179,789 B1 | * | 1/2001 | Tu et al. | ..................... 600/585 |
| 6,206,835 B1 | * | 3/2001 | Spillman, Jr. et al. | ...... 606/191 |
| 6,235,024 B1 | * | 5/2001 | Tu | ............................... 606/41 |
| 6,238,421 B1 | * | 5/2001 | Gunther et al. | ............... 607/13 |
| 6,267,781 B1 | * | 7/2001 | Tu | .............................. 607/113 |
| 6,272,370 B1 | * | 8/2001 | Gillies et al. | ................ 600/411 |

* cited by examiner

*Primary Examiner*—Gary Jackson
*Assistant Examiner*—(Jackie) Tan-Uyen T. Ho
(74) *Attorney, Agent, or Firm*—Benjamin Aaron Adler

(57) ABSTRACT

A stent device is provided. The stent device includes a helical structure. The stent device also includes a ring structure connected to the helical structure. The ring structure includes an inner conducting ring, an outer conducting ring, and a dielectric material disposed between the inner and outer conducting rings. The stent device radiates an induced electromagnetic field when subjected to an applied electromagnetic field.

29 Claims, 7 Drawing Sheets

MRI STENT

TECHNICAL FIELD

This invention relates to a stent used in conjunction with a magnetic resonance (MR) system, and more particularly to a stent which is capable of repeatedly ablating hyperplastic tissue growing around the stent when the stent is subjected to an RF electromagnetic field produced by an external scanner, thus preventing blockage of the stent.

BACKGROUND

Magnetic Resonance (MR) surface resonators are currently used in a variety of clinical and research applications. The purpose of a surface resonator is to provide improved signal-to-noise performance when imaging small regions. Typically, the resonator is placed on the surface of the body over the region of interest. The surface resonator can be used as a transmit/receive antenna, or, as in many applications, the volume resonator (sometimes referred to as a body coil) of the MR scanner will be used as the transmit antenna, while the surface resonator acts as the receive antenna to collect the MR signal from the desired region alone.

One area of concern when designing MR surface resonators for use as receive antennas is the decoupling issue. More specifically, if a surface resonator with the same resonant frequency as the transmit field is placed inside a volume resonator while the volume resonator is transmitting, the surface resonator will receive and retransmit an intense field around itself. This retransmitted field can result in RF burns to the patient. In order to prevent surface burns, the surface resonator is "decoupled" during the volume resonator transmit procedure. The surface resonator is decoupled by causing its resonant frequency to change during volume resonator transmit. A diode switching circuit is used to add an additional reactive element to the resonant circuit while transmit is taking place. For example, an additional inductor added to a resonant circuit will lower the resonant frequency. When the resonant frequency of the surface resonator is sufficiently far from the transmit frequency, the surface resonator will not receive and retransmit a signal, and the RF burn hazard is eliminated.

Known treatments for removing or preventing hyperplastic tissue located within an implanted stent body utilize invasive procedures, such as inserting a catheter into the area near the stent. The catheter is designed to include an antenna at its terminal end. The catheter can then be used as a radio frequency transmit path for ablating tissue that could otherwise create blockage within the vessel. However, such invasive procedures are significantly complex, present higher risks of post procedure complications and can be very uncomfortable for the patient. There are also limits on the number of catheter procedures which can be performed on a patient who is more susceptible to a hyperplastic response.

SUMMARY

In one aspect, the invention features a stent device. The stent device includes an electrically conductive helical structure. The stent device also includes an electrically conductive ring structure connected to the helical structure. The ring structure includes an inner conducting ring, an outer conducting ring, and a dielectric material disposed between the inner and outer conducting rings. The helical structure and the ring structure are arranged to produce an electromagnetic field when subjected to an applied electromagnetic field.

Embodiments may include one or more of the following features. The ring structure is connected to a first end of the helical structure, and further includes a second ring structure connected to a second, opposite end of the helical structure. The inner conducting ring, the outer conducting ring, and the dielectric material disposed between the inner and outer conducting rings are arranged for defining an electrical capacitor. The inner conducting rings of the ring structures are connected to the first end and the second end of the helical structure, respectively, and further include a return path conductor electrically interconnecting the first ring structure and the second ring structure. The return path conductor is connected to the outer conducting ring of each ring structure.

The helical structure defines a solenoidal inductor for conducting an electrical current. The helical structure and the ring structure define an electrically reactive circuit having a resonant frequency. The helical structure and the ring structure produce the electromagnetic field at the resonant frequency. In one configuration, the helical structure and the inner and outer conducting ring of each ring structure are formed from a nickel-titanium alloy. The nickel-titanium alloy comprises about 40% to 60% nickel.

In another aspect, the invention features a stent for implantation into a vessel of a body. The stent includes a solenoidal inductor formed by a helical wire structure and a capacitor is connected at each end of the inductor. A return path conductor electrically interconnects the capacitors. The inductor and the capacitor are arranged to radiate an electromagnetic field when subjected to an applied electromagnetic field.

Embodiments may include one or more of the following features. Each capacitor includes an inner conducting ring, an outer conducting ring, and a dielectric material disposed between the inner and outer conducting rings. The inner conducting rings of the capacitors are connected to a first end and a second end of the helical wire structure, respectively, and the return path conductor is connected to the outer conducting rings of the capacitors. The conductor is electrically connected in parallel with the capacitors. The inductor, the inner conducting ring and outer conducting ring of each capacitor, and the return path conductor are formed from a nickel-titanium wire structure. The inductor and the capacitors define an electrically reactive circuit having a resonant frequency. The applied electromagnetic field is transmitted by a magnetic resonance transmitter at the resonant frequency. The electrically reactive circuit radiates the electromagnetic field at the resonant frequency.

In another aspect, the invention features an RF reactive stent for implantation into a vessel of a body. The stent includes a solenoidal inductor for conducting an induced current. The inductor is formed from a helical wire structure having a first end and a second end. A first capacitor is connected to the first end of the inductor, and a second capacitor is connected to the second end of the inductor. A return path conductor electrically interconnects the first capacitor, the second capacitor and the solenoidal inductor as an electrically reactive circuit. The electrically reactive circuit forming the stent has a resonant frequency. The first capacitor, the second capacitor and the solenoidal inductor are arranged to generate an RF field when subjected to an applied RF field at the resonant frequency of the stent.

Embodiments may include one or more of the following features. The first and second capacitors are each formed by a ring structure having an inner conducting ring, an outer conducting ring, and a dielectric material disposed between the inner and outer conducting rings. The inductor, the first and second capacitors, and the return path conductor are coated with an insulating material. In one configuration, the insulating material is a polymer. The inductor, the inner and outer conducting rings of each capacitor, and the return path conductor are formed from a nickel-titanium wire structure.

In another aspect, the invention features a method for ablating tissue surrounding a reactive stent device. The method includes the steps of providing an RF reactive stent formed from a solenoidal inductor element which is electrically interconnected to a capacitor element. The method also includes implanting the stent within a vessel of a body, and irradiating the stent with an applied RF field for causing the inductor element and the capacitor element to generate an RF field in the vessel.

Embodiments may include one or more of the following features. The stent has a resonant frequency and the stent is irradiated by the applied RF field at the resonant frequency. The method includes the step of identifying the resonant frequency associated with the stent after the step of implanting the stent. The RF field generated by the inductor element and the capacitor element causes heating of tissue forming the vessel. The step of irradiating the stent produces a selected amount of heat sufficient to cause ablation of the tissue, which may be hyperplastic tissue surrounding the stent.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
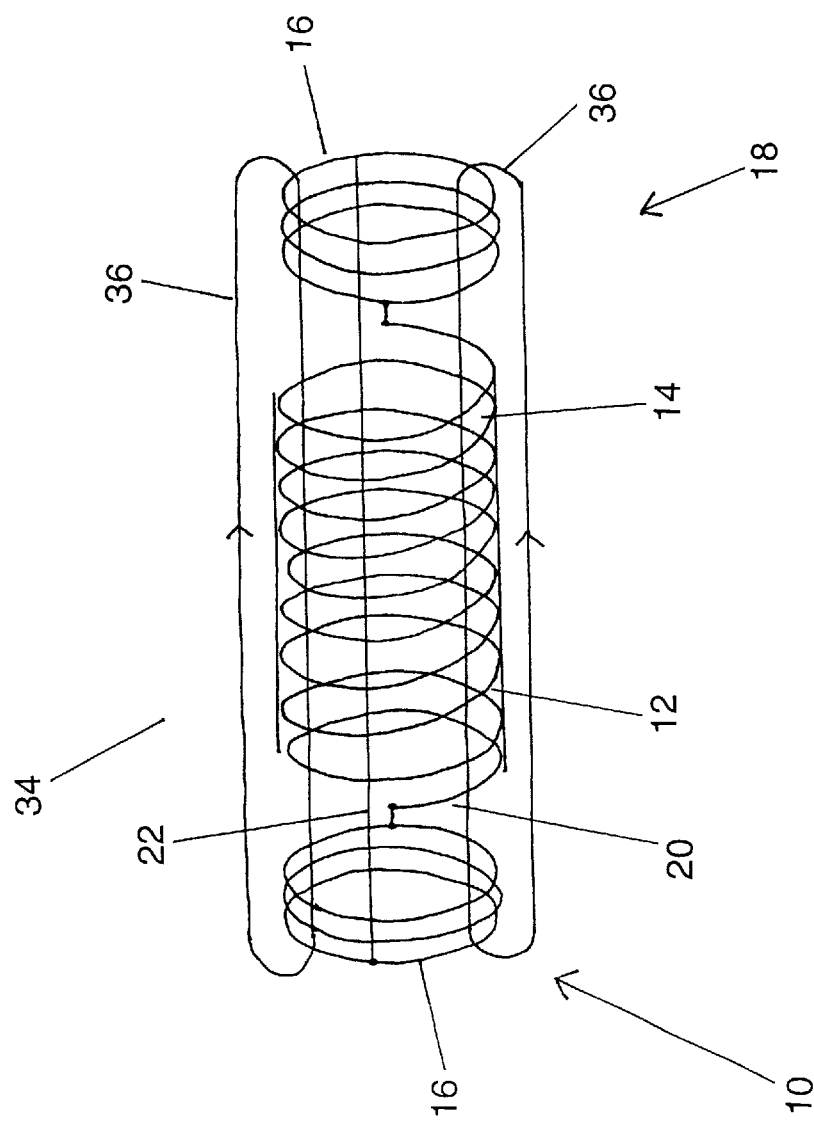
FIG. 1 is a perspective view showing the stent device along with the applied RF field and the induced RF field according to a preferred embodiment of the present invention.

Turning to FIG. 1, the RF reactive stent is shown. More specifically, the stent 10 includes a solenoidal body 12 having its geometry formed from a conducting wire 20 shaped into a generally helical cylindrical structure. The helical cylinder forming the stent body 12 prevents the collapse of the artery, vessel or passageway within which the stent is implanted, thereby promoting blood flow through the stent 10. The conducting wire 20 is made from a nickel-titanium (NiTi) alloy. The nickel-titanium alloy composition can range from about 40% to 60% nickel with the remaining percentage being titanium. The helical geometry of the solenoidal body 12 also forms an electrical inductor 14 having an inductance L. An electrical capacitor 16 is formed at each end of the inductor 14. The electrical capacitors 16 have capacitance values of $C_1$ and $C_2$. A return current path wire 22 connects each capacitor 16 with the inductor 14. As will be described in greater detail below, the capacitors 16 function to resonate the inductance of the solenoidal inductor 14. The resulting structure forms a resonant circuit 18 (FIG. 5A) which resonates when subjected to an applied RF electromagnetic field at the resonant frequency of the circuit 18. The applied electromagnetic field is generated at the resonant frequency of the circuit 18 which in turn re-radiates an electromagnetic field causing tissue surrounding the stent 10 to generate heat. This warming feature is described in greater detail below.

Figure 5A:
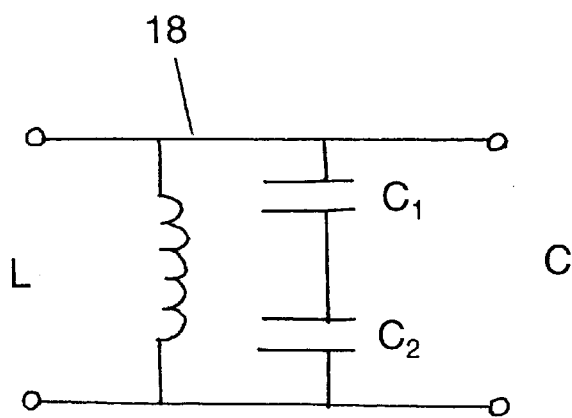
FIG. 5A is a schematic diagram showing the equivalent resonating circuit effected by the structure forming the stent device.

Referring briefly to FIG. 5A the equivalent circuit for the stent 10 can be modeled as a parallel LC resonant circuit. More specifically, the equivalent circuit 18 is shown as an inductor L, formed by the solenoidal body 12, in parallel with two capacitors 16 having capacitance values of $C_1$ and $C_2$. The resulting device is a parallel inductor/capacitor (LC) circuit 18 having a resonant frequency $f_r$ given by the following formula.

$$f_r = \frac{1}{2\pi\sqrt{L(C/2)}} \tag{1}$$

Figure 5B:
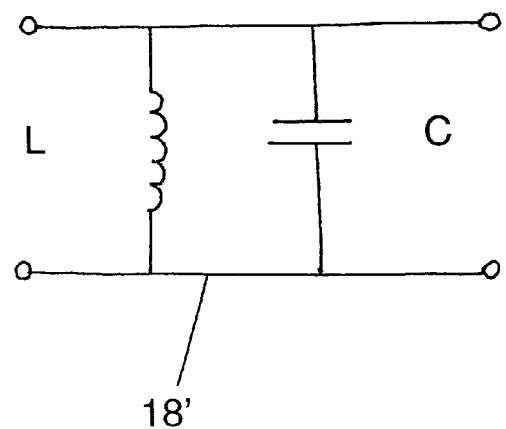
FIG. 5B is a schematic diagram showing the equivalent resonating circuit effected by an alternate structure forming the stent device.

The stent 10 is described above to include two capacitors 16, each capacitor being connected at one end of the inductor 14. However, as shown in FIG. 5B, the equivalent circuit 18' associated with stent 10 can be alternately configured to include only one capacitor C connected to the inductor L. In this alternate configuration the inner conductor ring 24 is connected to one end of the inductor 14, and the outer conductor ring 26 is connected to the opposite end of the inductor 14 via the return current wire 22. If a single capacitor 16 is used, the resonant frequency $f_r$ is given by:

$$f_r = \frac{1}{2\pi\sqrt{LC}} \tag{2}$$

in which case the return current path wire 22 is connected to the last coil forming the non-capacitive end of the stent body 12.

The resonant frequency $f_r$ is preferably selected such that it does not correspond to any clinical scanner frequencies, or harmonics thereof. Preferably, the resonant frequency $f_r$ will be established between 50 MHz to 300 MHz exclusive of 10 MHz ranges centered on the resonant frequencies used for clinical MR imaging from 1.5 T to 7.0 T. Exemplary values for L and C will depend on the size and application of the stent. Possible L and C values for a coronary stent circuit may be L=1.0 µH, C=0.5 pF, $f_r$=225 MHz wherein the values are in the range of L=0.3–1.2 µH and C=0.3–0.7 pF. Possible L and C values for a carotid stent circuit may be L=3.0 µH, C=0.8 pF, $f_r$=103 MHz wherein the values are in the range of L=1.0–4.0 µH and C=0.6–1.0 pF.

Figure 2:
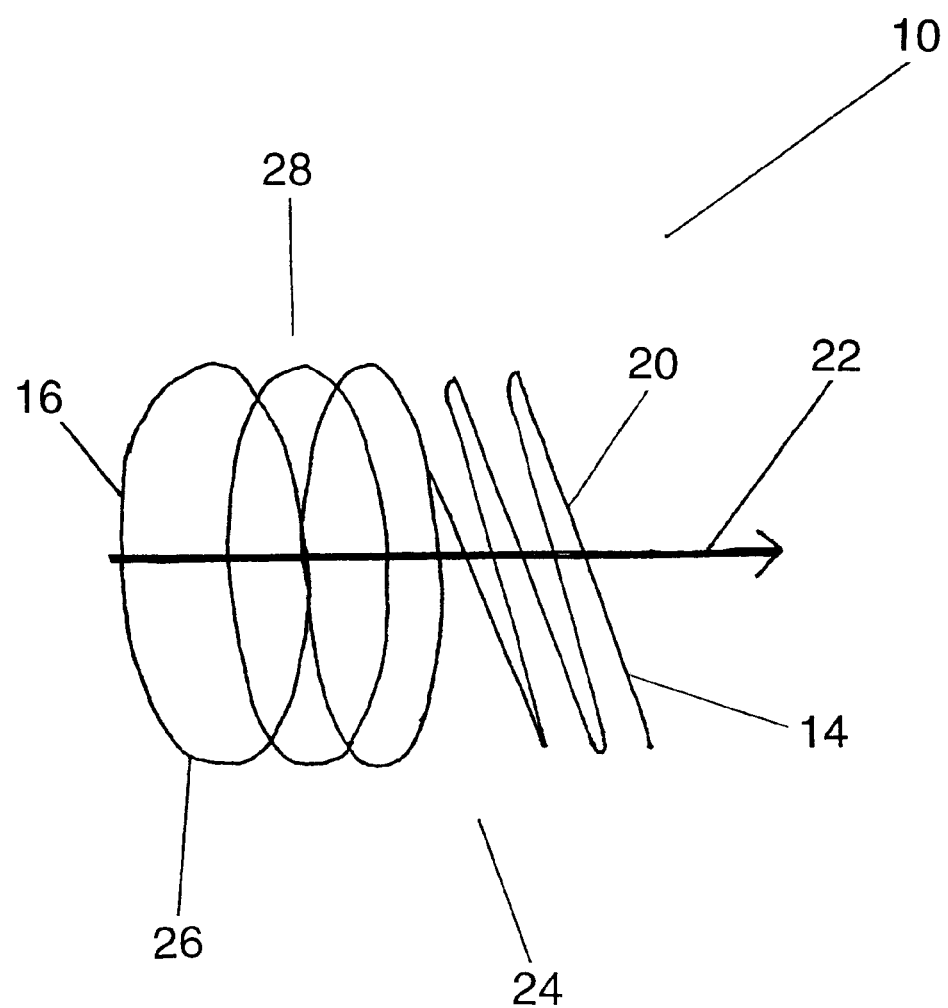
FIG. 2 is a perspective view showing the detailed structure of the stent body.

Referring to FIG. 2, the detailed structure of each capacitor 16 is shown. While only one capacitor 16 is shown in detail, it should be understood that each capacitor 16 is substantially similar in structure. The capacitor 16 formed at each end of the inductor 14 includes an inner conducting ring 24 and a structurally parallel outer conducting ring 26, each formed from the NiTi conducting wire 20. A polymer dielectric ring 28 is disposed between the inner and outer conducting rings 24, 26. The inner conducting ring 24 of each capacitor 16 is electrically connected to the last coil forming the end of the inductor 14, and preferably forms an integral structure with wire 20 that defines inductor 14. The outer conducting rings 26 of capacitors 16 are electrically interconnected by current path wire 22 thereby completing the LC electrical circuit.

Figure 3:
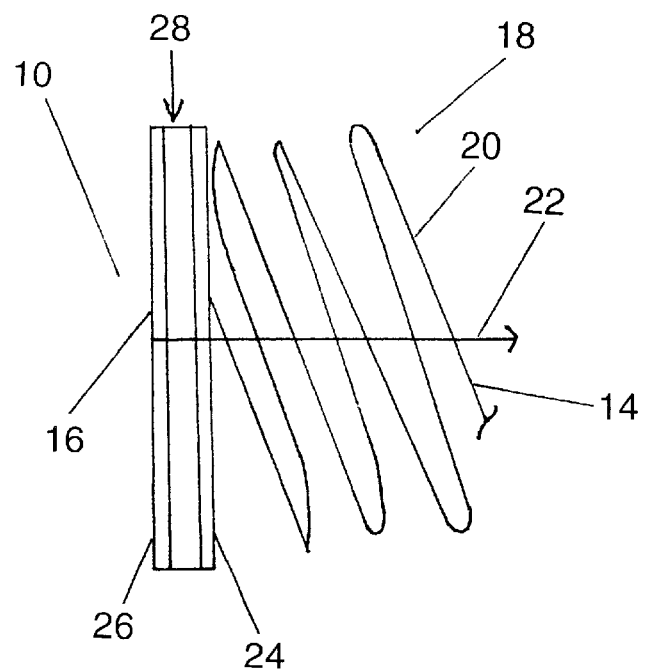
FIG. 3 is a side view of the stent of FIG. 2 showing the detailed structure of the capacitor portion of the stent.

A partial side view of the reactive stent structure 10 is shown in FIG. 3. More particularly, FIG. 3 shows the polymer dielectric ring 28 disposed between the inner and outer capacitive conductors 24, 26 for forming the electrical capacitor 16. The components forming the stent device 10 are also coated with an electrical insulator, in order to confine the induced electric current path to the conducting wire 20 of the stent body 10, and produce the desired radio frequency field geometry. More specifically, all of the NiTi conducting wire 20 forming the inductor 14, the return path conductor 22, and the capacitors 16 formed by the inner and outer conducting rings 24, 26 and the polymer dielectric ring 28, are coated with a suitable polymer material 32.

Figure 4:
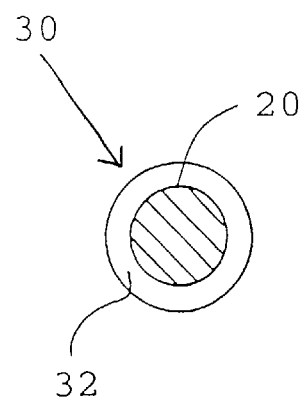
FIG. 4 is a cross-sectional view of the polymer coated wire forming the stent body.

Turning briefly to FIG. 4, the polymer coated wire 30 forming the structure of the stent device 10 is shown in cross-section. The diameter of the conducting wire 20 is in the range of about 0.007 in. to 0.013 in. As will be appreciated, the polymer coating 32 functions as an electrical insulator around the stent 10. The polymer coating 32 has a thickness in the range of about 50 to 400 microns. The polymer coating 32 is a photoreactive resin which can be applied by deposition techniques or by dipping, depending on the thickness and mechanical properties desired.

Referring back to FIG. 1, the functional aspects of the stent device 10 are described in more detail. In operation, when the stent device 10 is subjected to an applied RF field 34, the geometry of the inductor 14 and the capacitors 16 produces an intense induced RF field 36 around itself at the resonant frequency $f_r$. In order to generate the proper field geometry it is preferred that the electrical path be solenoidal. As such, this geometry allows for a highly focused induced RF field 36 near the stent body 12 that causes the tissue itself such as endothelial tissue in the immediate region of the stent 10 to generate heat by absorption of RF energy. This heating effect is responsible for the ablation of hyperplastic tissue around or within the stent 10.

Once in place, for example within an artery, the RF reactive stent device 10 is excited by placing the subject in a resonator designed for driving the stent 10 at its self-resonant frequency $f_r$. The transmitter of the resonator is turned on at a specific power level for a specified duration and transmits an RF signal at the resonant frequency of the stent device 10, causing the stent device 10 to resonate and produce the desired heating effect in the tissue. The stent device 10 functions to "receive" the RF signal and re-radiate an intense induced field 36 at the resonant frequency into its immediate surroundings. Absorption of RF energy from the re-radiated field by the vascular endothelium is intended to raise the temperature of the surrounding endothelial tissue to approximately 60° C. This temperature increase serves to ablate the surrounding tissue and to prevent further proliferation of the endothelial cells. The RF transmitter for generating the applied field 34 preferably includes a frequency source, an RF amplifier, and a resonator for producing the electromagnetic field. The resonator resembles an MR volume resonator and is driven by an RF amplifier of 500–1000 W output. An RF synthesizer is used as an adjustable frequency source in order to provide a signal at the resonant frequency $f_r$ of the implanted stent, which is then amplified and fed to the resonator.

As will be appreciated by one skilled in the art, it is important to know the exact resonant frequency of the stent 10 once it is implanted within the body. This is because the resonant frequency of the stent 10 will likely shift or change slightly after being implanted. Reasons for a resonant frequency shift include mechanical deformation of the stent, electric field losses in the conducting medium of blood and tissue, and dielectric effects of blood and tissue.

Figure 6:
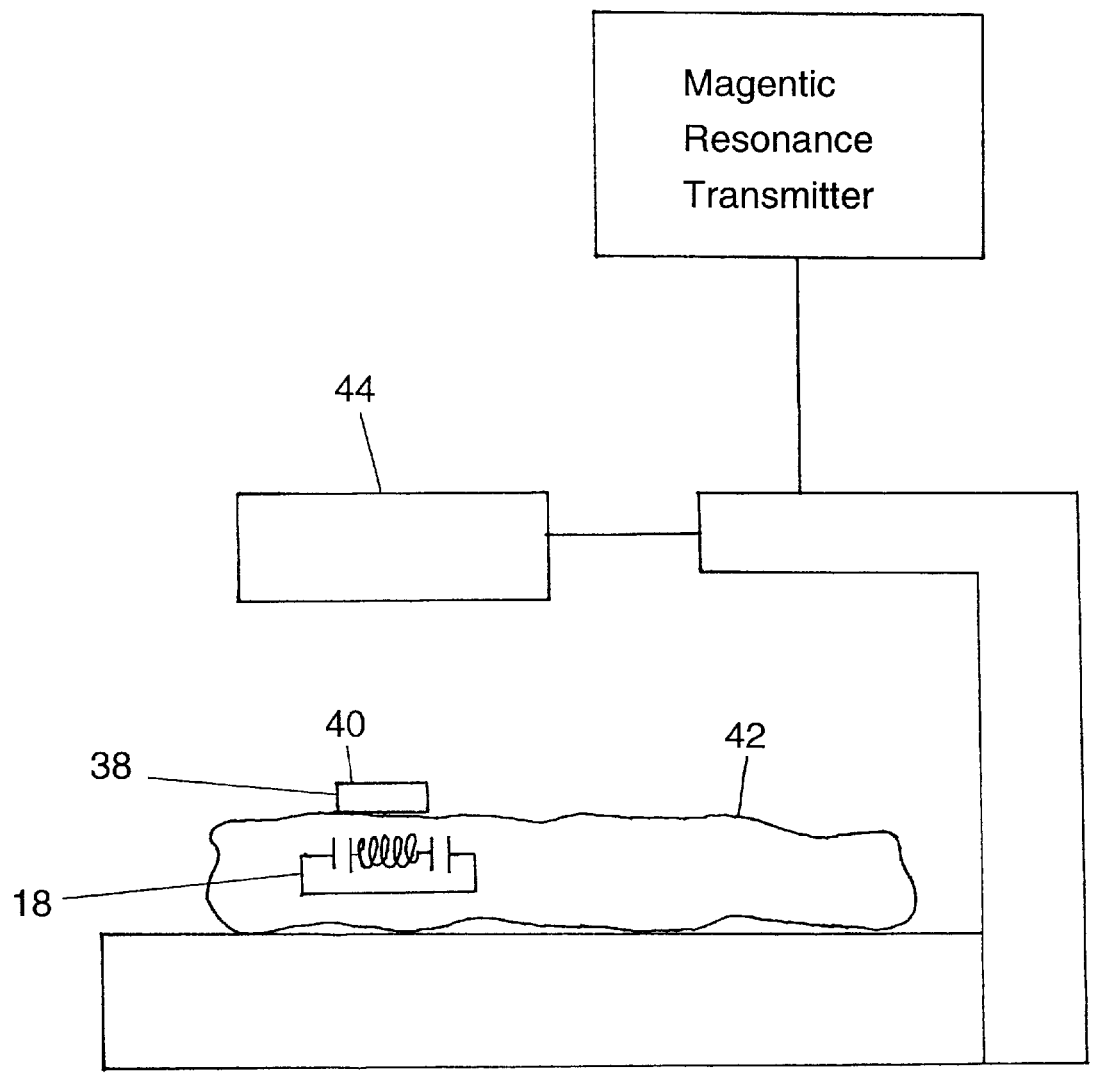
FIG. 6 is a schematic diagram showing a technique for determining the resonant frequency of the stent after implantation into the body of a patient.

Determining the resonant frequency is accomplished using an inductive coupling technique, and preferably using a device known as a "dip meter". This technique is described further with respect to FIG. 6. More specifically, FIG. 6 shows the stent 10 implanted within a patient's body 42. When the inductive loop 40 of the dip meter 38 is placed in proximity to a resonant circuit, such as the circuit 18 formed by the stent 10, and the meter 38 is tuned to the resonant frequency of the circuit 18, resonance is indicated by a change in the bias current of the oscillator associated with the dip meter 38, seen as a "dip" on the current meter. Thus, the operating frequency of the dip meter 38 can be varied to identify the unknown resonant frequency of the resonant circuit 18 formed by the stent 10 without physical or direct electrical contact with the stent 10. It should be noted that the applied RF field 34 is not present or utilized during the procedure of determining the resonant frequency of the implanted stent 10 using the dip meter 38. Further, the dip meter 38 is removed from the field of the transmit resonator 44 when the stent is irradiated by the applied RF field 34.

Figure 7:
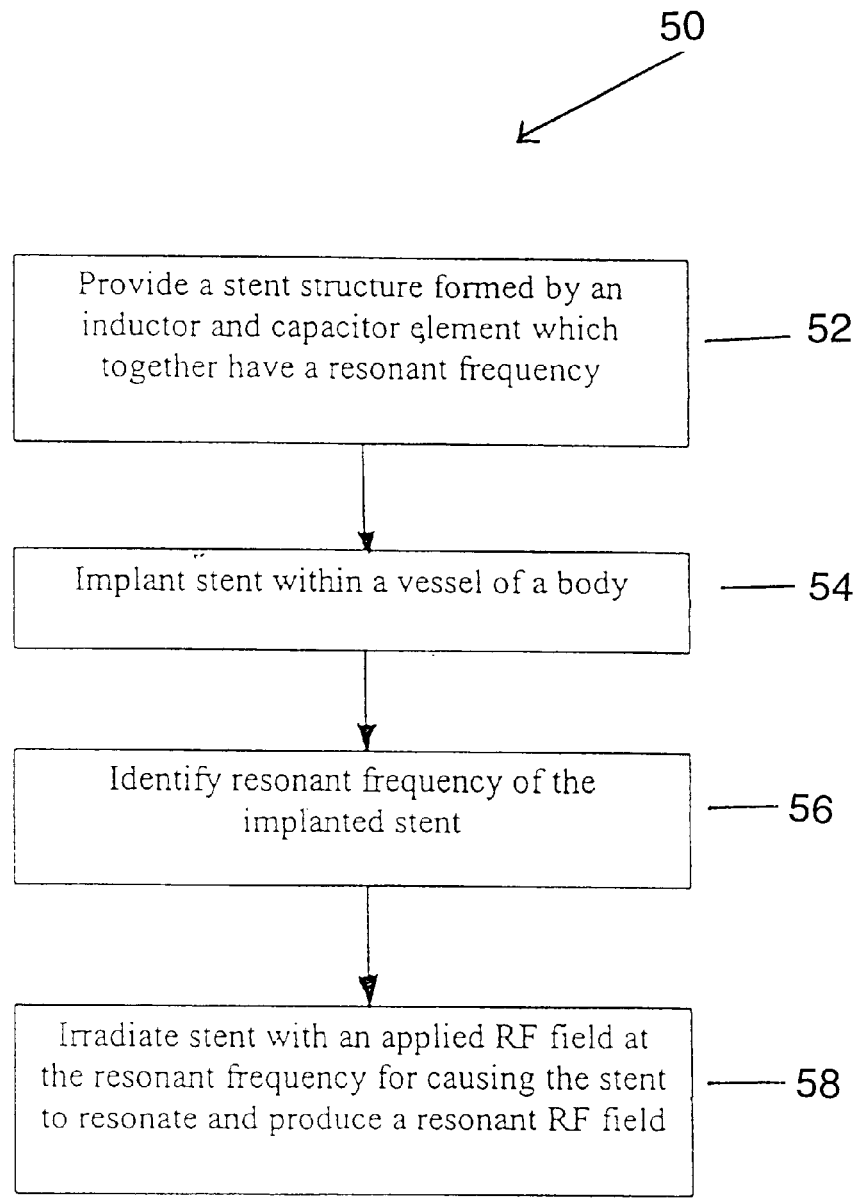
FIG. 7 is a flowchart showing a method for utilizing the stent.

With reference to FIG. 7, a method for ablating tissue either surrounding or within the stent device 10 is shown at 50. The method includes at 52 the step of providing an RF reactive stent 10 formed from a solenoidal inductor 14 and a capacitor 16 which together define an electrical circuit 18, 18'having a resonant frequency as described above. The stent device 10 is then implanted within a vessel of a body at 54. After the stent device is implanted, the resonant frequency of the stent device 10 is identified at 56. One technique for identifying the resonant frequency is through the use of a dip meter 38 as described above. The implanted stent device 10 is then irradiated at 58 with an applied RF electromagnetic field at the resonant frequency of the stent 10 which causes the stent to resonate and produce an induced RF field at the resonant frequency.

Figure 8:
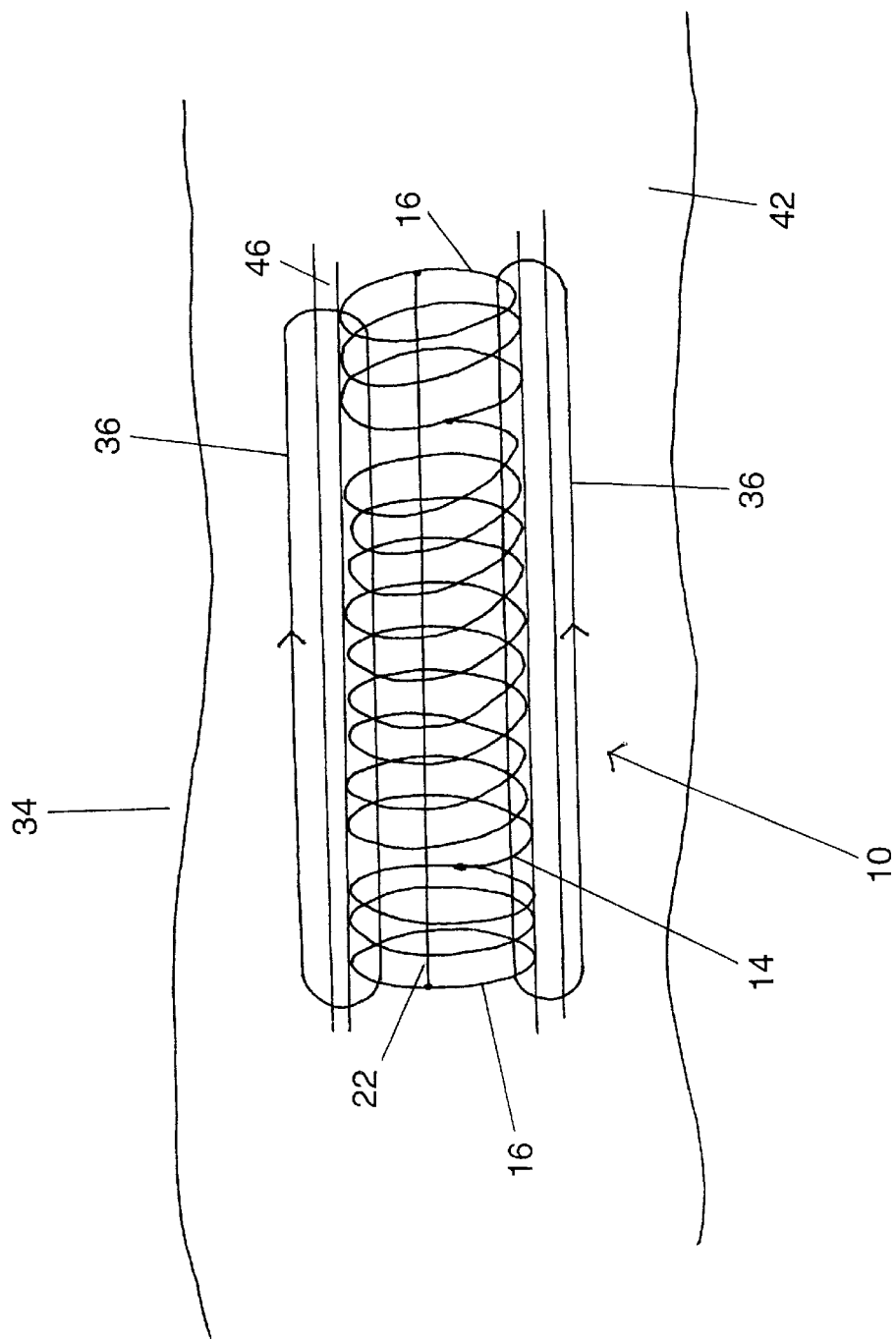
FIG. 8 is a diagram showing the electromagnetic field produced by the implanted stent.

Referring to FIG. 8, the stent device 10 is shown as being implanted within a vessel 46 of a body 42. Also shown is that after the resonant frequency is identified, the stent 10 is irradiated with the applied RF field 34 at the resonant frequency. As the stent 10 begins resonating, current begins conducting through the inductor 14 and capacitor 16 forming the stent 10, and the induced RF field 36 is produced. The induced RF field 36 then causes the tissue surrounding the stent 10 to generate heat for producing the desired ablation effect described above.

The stent device 10 of the present invention includes many advantages over known medical stents. The geometry of the stent device 10 results in the generation of an intense solenoidal RF electromagnetic field confined primarily to the vascular endothelium. For example, the stent device 10 allows tracking of blood flow post primary stent placement, and determination of any hyperplasic or restenotic response associated with the patient. The same stent device 10 can subsequently be used for producing an ablation field by using specific solenoidal geometry. Because the stent device 10 of the present invention is fully MR compatible, the stent 10 can be used for uniformly ablating the endothelium surrounding it, rather than ablating spots, as is currently done with ablation catheterization procedures. Thus, periodic re-ablation can be performed in a completely non-invasive manner.

The NiTi material forming the stent device 10 does not appear to produce any significant artifacting (signal loss) in the resulting MR images as do medical stents formed from stainless steel. As a result, the NiTi material allows the MR imaging system to image tissue surrounding the stent 10 and tissue inside the stent 10 without being blocked by the stent body 12. Accordingly, the NiTi structure forming the stent 10 provides many significant advantages over stent geometries formed from stainless steel which typically does not allow tissue within the stent to be imaged.

The stent 10 described herein may be utilized in a variety of therapeutic applications including but not limited to: shunts, shunts used for dialysis, artificial veins, arteries and grafts, esophageal stenosis, esophageal cancer, esophageal varacies, lung bronchi for cancer treatment, urethra, hydrocephalus shunt tubes, trachea, middle ear tubes, lymphatic ducts and grafts, gastrointestinal stenosis and inflammatory diseases (e.g. Crohn's disease), pyloric stenosis, and biliary atresia.

A number of embodiments of the invention have been described. Nevertheless, it will be understood that various modifications may be made without departing from the spirit and scope of the invention. Accordingly, other embodiments are within the scope of the following claims.

What is claimed is:

1. A stent device comprising:
   an electrically conductive helical structure; and
   an electrically conductive ring structure connected to the helical structure, the ring structure including an inner conducting ring, an outer conducting ring, and a dielectric material disposed between the inner and outer conducting rings;
   the helical structure and the ring structure being arranged to produce an electromagnetic field when subjected to an applied electromagnetic field.

2. The stent device of claim 1 wherein said ring structure is connected to a first end of the helical structure, and further comprising a second said ring structure connected to a second, opposite end of the helical structure.

3. The stent device of claim 1 wherein the inner conducting ring, the outer conducting ring, and the dielectric material disposed between the inner and outer conducting rings define an electrical capacitor.

4. The stent device of claim 2 wherein the inner conducting rings of said ring structures are connected to said first end and said second end of said helical structure, respectively, and further including a return path conductor electrically interconnecting the first said ring structure and the second said ring structure.

5. The stent device of claim 4 wherein the return path conductor is connected to the outer conducting ring of each said ring structure.

6. The stent device of claim 1 wherein the helical structure defines a solenoidal inductor for conducting an electrical current.

7. The stent device of claim 1 wherein the helical structure and the ring structure define an electrically reactive circuit having a resonant frequency.

8. The stent device of claim 7 wherein the helical structure and the ring structure produce the electromagnetic field at the resonant frequency.

9. The stent device of claim 2 wherein the helical structure and the inner and outer conducting ring of each ring structure are formed from a nickel-titanium alloy.

10. The stent device of claim 9 wherein the nickel-titanium alloy comprises about 40% to 60% nickel.

11. A stent for implantation into a vessel of a body comprising:
    a solenoidal inductor formed by a helical wire structure;
    a capacitor connected at each end of the inductor; and
    a return path conductor electrically interconnecting the capacitors;
    the inductor and the capacitor being arranged to radiate an electromagnetic field when subjected to an applied electromagnetic field.

12. The stent of claim 11 wherein each said capacitor includes an inner conducting ring, an outer conducting ring, and a dielectric material disposed between the inner and outer conducting rings.

13. The stent of claim 12 wherein the inner conducting rings of said capacitors are connected to a first end and a second end of the helical wire structure, respectively, and the return path conductor is connected to the outer conducting rings of said capacitors.

14. The stent of claim 13 wherein the inductor is electrically connected in parallel with said capacitors.

15. The stent of claim 14 wherein the inductor, the inner conducting ring and outer conducting ring of each capacitor, and the return path conductor are formed from a nickel-titanium wire structure.

16. The stent of claim 11 wherein the inductor and the capacitors define an electrically reactive circuit having a resonant frequency.

17. The stent of claim 16 wherein the applied electromagnetic field is transmitted by a magnetic resonance transmitter at the resonant frequency.

18. The stent of claim 16 wherein the electrically reactive circuit radiates the electromagnetic field at the resonant frequency.

19. An RF reactive stent for implantation into a vessel of a body comprising:
    a solenoidal inductor for conducting an induced current, the inductor being formed from a helical wire structure having a first end and a second end;
    a first capacitor connected to the first end of the inductor;
    a second capacitor connected to the second end of the inductor;
    a return path conductor electrically interconnecting the first capacitor, the second capacitor and the solenoidal inductor as an electrically reactive circuit having a resonant frequency;
    the first capacitor, the second capacitor and the solenoidal inductor being arranged to generate an RF field when subjected to an applied RF field at the resonant frequency of the stent.

20. The stent of claim 19 wherein the first and second capacitors are each formed by a ring structure having an inner conducting ring, an outer conducting ring, and a dielectric material disposed between the inner and outer conducting rings.

21. The stent of claim 19 wherein the inductor, the first and second capacitors, and the return path conductor are coated with an insulating material.

22. The stent of claim 21 wherein the insulating material is a polymer.

23. The stent of claim 20 wherein the inductor, the inner and outer conducting rings of each capacitor, and the return path conductor are formed from a nickel-titanium wire structure.

24. A method for ablating tissue surrounding a reactive stent device comprising:

providing an RF reactive stent formed from a solenoidal inductor element electrically interconnected to a capacitor element;

implanting the stent within a vessel of a body; and irradiating the stent with an applied RF field to cause the inductor element and the capacitor element to generate an RF field in the vessel.

25. The method of claim 24 wherein the stent has a resonant frequency and the stent is irradiated by the applied RF field at the resonant frequency.

26. The method of claim 25 further including the step of identifying the resonant frequency associated with the stent after the step of implanting the stent.

27. The method of claim 24 wherein the RF field generated by the inductor element and the capacitor element causes heating of tissue forming the vessel.

28. The method of claim 27 wherein the step of irradiating the stent device produces a selected amount of heat sufficient to cause ablation of the tissue.

29. The method of claim 28 wherein the tissue is hyperplastic tissue.

* * * * *